US006552037B2

(12) United States Patent
Cai et al.

(10) Patent No.: US 6,552,037 B2
(45) Date of Patent: Apr. 22, 2003

(54) 2-SUBSTITUTED IMIDAZO[1,2-A]PYRIDINE DERIVATIVES

(75) Inventors: Guolin Cai, Thousand Oaks, CA (US); Kenneth Shaw, Weston, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/897,837

(22) Filed: Jun. 29, 2001

(65) Prior Publication Data

US 2002/0032200 A1 Mar. 14, 2002

Related U.S. Application Data

(60) Provisional application No. 60/215,646, filed on Jun. 30, 2000.

(51) Int. Cl.[7] .................. C07D 471/04; C07D 49/02; A61K 31/44
(52) U.S. Cl. .................. 514/303; 546/118; 546/121; 514/300
(58) Field of Search ............... 546/118, 121; 514/303, 300

(56) References Cited

U.S. PATENT DOCUMENTS 4,460,592 A    7/1984    Kaplan et al. ............... 424/256

FOREIGN PATENT DOCUMENTS

| EP | 0 050 563 | 4/1982 |
| EP | 0 172 096 | 2/1986 |
| FR | 1536351 | * 8/1968 |
| WO | WO 96/25414 | 8/1996 |

OTHER PUBLICATIONS

CAS printout for Kaplan (EP 92459).*
CAS printout for Sahu, J. India Chem. 1985.*
Enguehard, et al., (2000) *Chem. Pharm. Bull.* 48(7):935–940.
Gupta, et al., (1998) *Bioorg. Med. Chem.* 6:2213–2218.
Trapani, et al., (1997) *J. Med. Chem.* 40:3109–3118.

* cited by examiner

*Primary Examiner*—Bruck Kifle
*Assistant Examiner*—Hong Liu
(74) *Attorney, Agent, or Firm*—McDonnell Boehnen Hulbert & Berghoff

(57) ABSTRACT

Disclosed are compounds of the formula:

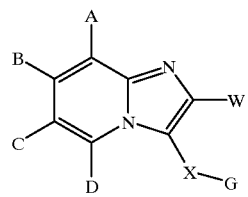

and the pharmaceutically acceptable salts, prodrugs and solvates thereof, wherein X, A, B, C, D and W are defined herein, which compounds bind with high selectivity and high affinity to the benzodiazepine site of the $GABA_A$ receptors and are therefore useful in the treatment of certain central nervous system (CNS) diseases and as probes for the localization of $GABA_A$ receptors in tissue samples.

25 Claims, No Drawings

2-SUBSTITUTED IMIDAZO[1,2-A]PYRIDINE DERIVATIVES

BACKGROUND OF THE INVENTION

This application claims priority from U.S. Provisional Application S.N. 60/215,646, filed Jun. 30, 2000, the disclosure of which is incorporated herein in its entirety.

FIELD OF THE INVENTION

This invention relates to 2-phenylimidazo[1,2-a]pyridine derivatives and more specifically to such compounds that bind with high selectivity and high affinity to the benzodiazepine site of $GABA_A$ receptors. This invention also relates to pharmaceutical compositions comprising such compounds and to the use of such compounds in treatment of certain central nervous system (CNS) diseases.

DESCRIPTION OF THE RELATED ART

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits. Evidence such as message distribution, genome localization and biochemical study results suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$.

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th}$ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of certain other CNS active compounds. For example, there is evidence that selective serotonin reuptake inhibitors (SSRIs) may show greater antidepressant activity when used in combination with $GABA_A$ selective ligands than when used alone.

U.S. Pat. No. 4,460,592 discloses imidazo[1,2-a]pyridine derivatives.

SUMMARY OF THE INVENTION

Disclosed are certain novel compounds, particularly 2-phenylimidazo[1,2-a]pyridine derivatives that bind to cell surface receptors. Preferred compounds of the invention bind to GABA receptors, in particular these compounds possess affinity for the benzodiazepine site of $GABA_A$ receptors, including human $GABA_A$ receptors. Also preferred are compounds that exhibit high selectivity to the benzodiazepine site of the $GABA_A$ receptor. These compounds are therefore considered to be of potential use in the treatment of a broad array of diseases or disorders in patients, which are characterized by modulation of $GABA_A$ receptors.

Such diseases or disorders include, but are not limited to depression, anxiety, sleep disorders, cognitive disorders, low alertness, psychosis, obesity, pain, Parkinson's disease, Alzheimer's disease, neurodegenerative diseases, movement disorders, Down's syndrome, and benzodiazepine overdoses.

Thus, the invention provides novel compounds of Formula I (shown below), and pharmaceutical compositions comprising compounds of Formula I.

The invention further comprises methods of treating patients suffering from certain CNS disorders with a therapeutically effective amount of a compound of the invention. The patient may be a human or other mammal. Treatment of humans, domesticated companion animals (pet) or livestock animals suffering from certain CNS disorders with a therapeutically effective amount of a compound of the invention is encompassed by the invention.

In a separate aspect, the invention provides a method of potentiating the actions of other CNS active compounds. This method comprises administering a therapeutically effective amount of a compound of the invention with another CNS active compound.

Additionally this invention relates to the use of the compounds of the invention as probes for the localization of $GABA_A$ receptors in tissue sections.

Accordingly, a broad aspect of the invention is directed to compounds of Formula I:

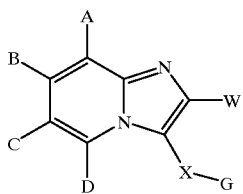

Formula I the pharmaceutically acceptable salts or solvates thereof, wherein A, B, C, D, G, W, and X are defined below.

In another aspect, the invention provides intermediates useful for preparing the compounds of Formula I.

In a further aspect, the invention provides methods for making compounds of Formula I.

DETAILED DESCRIPTION OF THE INVENTION

The invention is directed to compounds and pharmaceutically acceptable salts, prodrugs, and solvates of Formula I the formula:

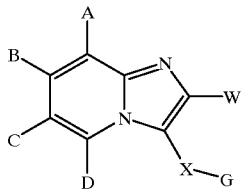

or a pharmaceutically acceptable salt thereof, wherein:
A, B, C, and D independently represent
  i) hydrogen, hydroxy, halogen, cyano, nitro,
  ii) $C_1$–$C_6$ alkyl optionally substituted independently with one, two, or three of $R_a$,
  iii) $C_2$–$C_6$ alkenyl optionally substituted independently with one, two, or three of $R_a$,
  iv) $C_2$–$C_6$ alkynyl optionally substituted independently with one, two, or three of $R_a$,
  v) $C_1$–$C_6$ alkoxy optionally substituted independently with one, two, or three of $R_a$,
  vi) alkylthio optionally substituted independently with one, two, or three of $R_a$,
  vii) alkylsulfinyl wherein the alkyl portion is optionally substituted independently with one, two, or three of $R_a$,
  viii) alkylsulfonyl wherein the alkyl portion is optionally substituted independently with one, two, or three of $R_a$,
  ix) —$NR_3R_4$, wherein $R_3$ and $R_4$ are independently hydrogen, $C_1$–$C_6$ alkyl, $C_3$–$C_7$ cycloalkyl, or $C_3$–$C_7$ cycloalkyl($C_1$–$C_6$)alkyl, and
  x) —$NR_3R_4$, wherein $R_3$ and $R_4$ are joined to form a heterocyclic ring having from 3–7 members, wherein
  where $R_a$ is independently selected at each occurrence from halogen, hydroxy, $C_1$–$C_6$ alkoxy, nitro, cyano, amino, or oxo,
G is heteroaryl or heterocycloalkyl, optionally substituted with up to three groups independently selected from
  i) halogen, halo($C_1$–$C_6$)alkyl, hydroxy, nitro, cyano,
  ii) arylalkyl, wherein the aryl portion of the arylalkyl moiety is optionally substituted with one, two, or three groups which are independently selected from halogen, nitro, cyano, hydroxy, halo($C_1$–$C_6$)alkyl, amino, mono- and di-alkyl($C_1$–$C_6$)amino,
  iii) —$NR_5R_6$ wherein $R_5$ and $R_6$ are the same or different and independently represent hydrogen, alkoxyalkyl, or $C_1$–$C_6$ alkyl substituted with —$(CH_2)_m$—$NR_7R_8$, wherein m is 0 or an integer of from 1 to 6 and $R_7$ and $R_8$ are the same or different and represent hydrogen, $C_1$–$C_6$ alkyl, $C_3$–$C_7$ cycloalkyl, or $C_3$–$C_7$ cycloalkyl ($C_1$–$C_6$)alkyl, and
  iv) $C_1$–$C_6$ alkyl and $C_1$–$C_6$ alkoxy, each of which is optionally substituted with one or two of $R_b$, and
  v) heterocycloalkyl optionally substituted with up to three groups which are independently selected from halogen, hydroxy, nitro, cyano, halo($C_1$–$C_6$)alkyl, $C_1$–$C_6$alkyl, ($C_1$–$C_6$)alkoxy, ($C_1$–$C_6$)alkoxy($C_1$–$C_6$)alkyl, ($C_1$–$C_6$) alkoxy($C_1$–$C_6$) alkoxy, ($C_3$–$C_7$) cycloalkyl ($C_1$–$C_6$) alkoxy, cycloalkyl ($C_1$–$C_6$)alkyl, hydroxy($C_1$–$C_6$) alkyl, hydroxy($C_1$–$C_6$) alkoxy, amino ($C_1$–$C_6$) alkyl, and phenyl;
W is phenyl or pyridyl, each of which is optionally substituted with one, two, or three groups which are independently selected from
  i) halogen, nitro, cyano, hydroxy, halo($C_1$–$C_6$)alkyl, amino, mono- and di-($C_1$–$C_6$)alkylamino,
  ii) $C_1$–$C_6$ alkyl and $C_1$–$C_6$ alkoxy, each of which is optionally substituted with one or two of $R_c$, $R_b$ and $R_c$ are independently selected at each occurrence from
    i) hydroxy, $C_1$–$C_6$alkoxy, $C_3$–$C_7$cycloalkyl, $C_3$–$C_7$cycloalkyl($C_1$–$C_6$)alkoxy, heterocycloalkyl,
    ii) —$(CH_2)x$—$NR_9R_{10}$, wherein x is 0 or an integer of 1 to 6, and $R_9$ and $R_{10}$ are the same or different and represent hydrogen, $C_1$–$C_6$ alkyl, $C_3$–$C_7$cycloalkyl, or $C_3$–$C_7$ cycloalkyl($C_1$–$C_6$)alkyl, and
    iii) —$NR_9R_{10}$, where $R_9$ and $R_{10}$ are joined to form a heterocyclic ring having from 3–7 members; and
X is O, NH, N($C_1$–$C_6$ alkyl), S, $SO_2$, or $(CH2)_n$, wherein n is 1, 2, 3, or 4.

Preferred compounds and salts of the invention include those where G is selected from imidazolyl, imidazolinyl, imidazopyridinyl, imdazopyrimidinyl, imidazopyrazinyl, and benzimidazolyl each of which is optionally substituted with up to three groups as described above for Formula I. Such compounds and salts will be described herein as compounds and salts of Formula IA.

Particularly preferred G groups include 2-imidazolyl, 2-imidazolinyl, 2-imidazopyridinyl, 2-imdazopyrimidinyl, 2-imidazopyrazinyl, or 2-benzimidazolyl, each of which is optionally substituted as described herein. Specific G groups include 2-imidazolyl, 2-imidazolinyl, 2-imidazo[4,5-c]pyridinyl, 2-imidazo[4,5-b]pyridinyl, 2-imidazo[4,5-d]pyrimidinyl, 2-imidazo[4,5-b]pyrazinyl, or 2-benzimidazolyl, each of which is optionally substituted with halogen, halo($C_1$–$C_6$)alkyl, hydroxy, nitro, cyano, amino or mono- or di($C_1$–$C_6$)alkylamino, amino($C_1$–$C_6$) alkyl, or mono- or di($C_1$–$C_6$)alkylamino($C_1$–$C_6$)alkyl, $C_1$–$C_6$ alkyl or $C_1$–$C_6$ alkoxy.

The invention is particularly directed to compounds and salts of Formula II

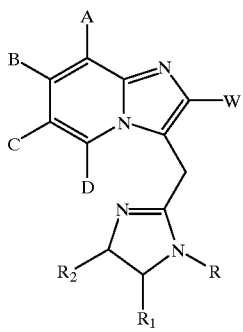

Formula II wherein
A, B, C, D and W are as defined for Formula IA;
R represents hydrogen, $C_1$–$C_6$ alkyl, or $C_3$–$C_7$ cycloalkyl; and
$R_1$ and $R_2$ independently represent hydrogen, halogen, $C_1$–$C_6$alkyl, or $C_1$–$C_6$alkoxy.

A particular embodiment of the invention includes compounds of Formula II (or the pharmaceutically acceptable salts thereof) of Formual IIA

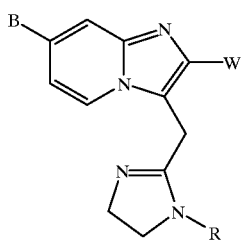

Formula IIA wherein:

B represents hydrogen, halogen, $C_1$–$C_3$ alkyl, or $C_1$–$C_3$ alkoxy;

W is phenyl or pyridyl each of which is optionally substituted with 1 or 2 groups independently selected from the group consisting of halogen, halo($C_1$–$C_6$)alkyl, hydroxy, amino, $C_1$–$C_6$ alkyl, $C_1$–$C_6$ alkoxy, and mono and di-($C_1$–$C_3$)alkylamino; and R represents hydrogen, $C_1$–$C_6$ alkyl, or $C_3$–$C_7$ cycloalkyl.

The invention is further directed to compounds and salts of Formula III:

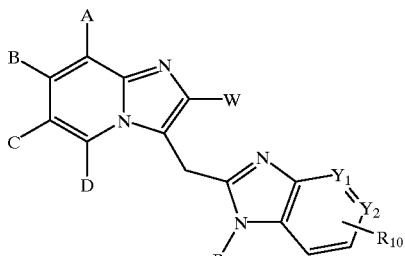

Formula III wherein:

A, B, C, D, and W are as defined for Formula IA;
R represents hydrogen, $C_1$–$C_6$ alkyl, or $C_3$–$C_7$ cycloalkyl;
$R_{10}$ represents 0, 1, or 2 groups independently selected from
  i) halogen, halo($C_1$–$C_6$)alkyl, hydroxy, nitro, cyano,
  ii) arylalkyl, wherein the aryl portion of the arylalkyl moiety is optionally substituted with one, two, or three groups which are independently selected from halogen, nitro, cyano, hydroxy, halo ($C_1$–$C_6$) alkyl, amino, mono- and di-alkyl($C_1$–$C_6$)amino,
  iii) —$NR_5R_6$ wherein $R_5$ and $R_6$ are the same or different and independently represent hydrogen, alkoxyalkyl, or $C_1$–$C_6$ alkyl substituted with —$(CH_2)_m$—$NR_7R_8$, wherein m is 0 or an integer of from 1 to 6 and $R_7$ and $R_8$ are the same or different and represent hydrogen, $C_1$–$C_6$ alkyl, $C_3$–$C_7$ cycloalkyl, or $C_3$–$C_7$ cycloalkyl ($C_1$–$C_6$)alkyl, and
  iv) $C_1$–$C_6$ alkyl and $C_1$–$C_6$ alkoxy, each of which is optionally substituted with one or two of $R_b$, and
  v) heterocycloalkyl optionally substituted with up to three groups which are independently selected from halogen, hydroxy, nitro, cyano, halo($C_1$–$C_6$)alkyl, $C_1$–$C_6$alkyl, ($C_1$–$C_6$)alkoxy, ($C_1$–$C_6$)alkoxy($C_1$–$C_6$)alkyl, ($C_1$–$C_6$) alkoxy($C_1$–$C_6$)alkoxy, ($C_3$–$C_7$) cycloalkyl ($C_1$–$C_6$) alkoxy, cycloalkyl ($C_1$–$C_6$) alkyl, hydroxy($C_1$–$C_6$) alkyl, hydroxy($C_1$–$C_6$)alkoxy, amino($C_1$–$C_6$)alkyl, and phenyl;

$Y_1$ and $Y_2$ represent CH or N, with the proviso that not both $Y_1$ and $Y_2$ are N.

Another particular embodiment of the invention includes compounds of Formula III (or the pharmaceutically acceptable salts thereof) of Formula IIIA

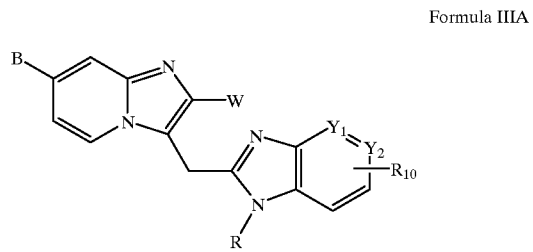

Formula IIIA wherein:

B is hydrogen, halogen, $C_1$–$C_3$ alkyl, or $C_1$–$C_3$ alkoxy;
R represents hydrogen, $C_1$–$C_6$ alkyl, or $C_3$–$C_7$ cycloalkyl;
$R_{10}$ is hydrogen, halogen, halo($C_1$–$C_6$)alkyl, hydroxy, amino, $C_1$–$C_6$ alkyl, $C_1$–$C_6$ alkoxy, or mono or di-($C_1$–$C_3$)alkylamino;
W is phenyl or pyridyl each of which is optionally substituted with 1 or 2 groups independently selected from the group consisting of halogen, halo($C_1$–$C_6$)alkyl, hydroxy, amino, $C_1$–$C_6$ alkyl, $C_1$–$C_6$ alkoxy, and mono and di-($C_1$–$C_3$) alkylamino; and
$Y_1$ and $Y_2$ represent CH or N, with the proviso that not both $Y_1$ and $Y_2$ are N.

Also included in the invention are compounds and salts of Formula IV

Formula IV

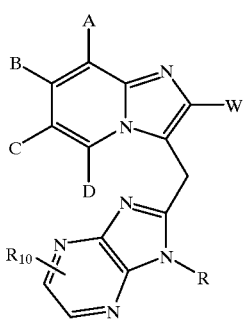

wherein:
A, B, C, D, and W are as defined for Formula IVA;
R represents hydrogen, $C_1$–$C_6$ alkyl, or $C_3$–$C_7$ cycloalkyl; and
$R_{10}$ represents 0, 1, or 2 groups independently selected from
 i) halogen, halo($C_1$–$C_6$)alkyl, hydroxy, nitro, cyano,
 ii) arylalkyl, wherein the aryl portion of the arylalkyl moiety is optionally substituted with one, two, or three groups which are independently selected from halogen, nitro, cyano, hydroxy, halo($C_1$–$C_6$)alkyl, amino, mono- and di-alkyl($C_1$–$C_6$)amino,
 iii) —$NR_5R_6$ wherein $R_5$ and $R_6$ are the same or different and independently represent hydrogen, alkoxyalkyl, or $C_1$–$C_6$ alkyl substituted with —$(CH_2)_m$—$NR_7R_8$, wherein m is 0 or an integer of from 1 to 6 and $R_7$ and $R_8$ are the same or different and represent hydrogen, $C_1$–$C_6$ alkyl, $C_3$–$C_7$ cycloalkyl, or $C_3$–$C_7$ cycloalkyl ($C_1$–$C_6$) alkyl, and
 iv) $C_1$–$C_6$ alkyl and $C_1$–$C_6$ alkoxy, each of which is optionally substituted with one or two of $R_b$, and
 v) heterocycloalkyl optionally substituted with up to three groups which are independently selected from halogen, hydroxy, nitro, cyano, halo($C_1$–$C_6$)alkyl, $C_1$–$C_6$alkyl, ($C_1$–$C_6$)alkoxy, ($C_1$–$C_6$)alkoxy($C_1$–$C_6$)alkyl, ($C_1$–$C_6$) alkoxy, ($C_3$–$C_7$) cycloalkyl ($C_1$–C6)alkoxy, cycloalkyl ($C_1$–C6) alkyl, hydroxy($C_1$–$C_6$)alkyl, hydroxy($C_1$–$C_6$) alkoxy, amino($C_1$–$C_6$)alkyl, and phenyl.

Another embodiment of the invention is represented compounds of Formula IV (or the pharmaceutically acceptable salts thereof) of Formula IVA

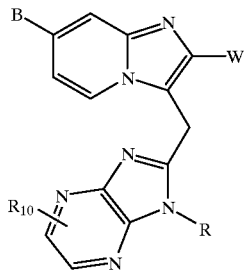

wherein:
B is hydrogen, halogen, $C_1$–$C_3$ alkyl, or $C_1$–C3 alkoxy;
R represents hydrogen, $C_1$–$C_6$ alkyl, or $C_3$–$C_7$ cycloalkyl;
$R_{10}$ is hydrogen, halogen, halo($C_1$–$C_6$)alkyl, hydroxy, amino, $C_1$–$C_6$ alkyl, $C_1$–$C_6$ alkoxy, or mono or di-($C_1$–$C_3$)alkylamino; and
W is phenyl or pyridyl each of which is optionally substituted with 1 or 2 groups independently selected from the group consisting of halogen, halo($C_1$–$C_6$)alkyl, hydroxy, amino, $C_1$–$C_6$ alkyl, $C_1$–$C_6$ alkoxy, and mono and di-($C_1$–$C_3$) alkylamino.

The invention also included compounds and salts of Formula V

Formula V

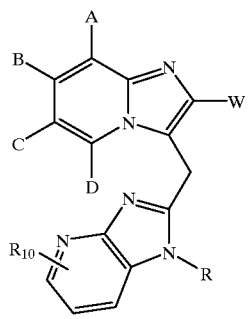

wherein

R represents hydrogen, $C_1$–$C_6$ alkyl, or $C_3$–$C_7$ cycloalkyl;
$R_{10}$ is hydrogen, halogen, halo($C_1$–$C_6$)alkyl, hydroxy, amino, $C_1$–$C_6$ alkyl, $C_1$–$C_6$ alkoxy, or mono or di-($C_1$–$C_3$)alkylamino; and
W is phenyl or pyridyl each of which is optionally substituted with 1 or 2 groups independently selected from the group consisting of halogen, halo($C_1$–$C_6$)alkyl, hydroxy, amino, $C_1$–$C_6$ alkyl, $C_1$–$C_6$ alkoxy, and mono and di-($C_1$–$C_3$) alkylamino.

Representative compounds of Formula I are shown below in Table 1.

TABLE 1

Compound 1

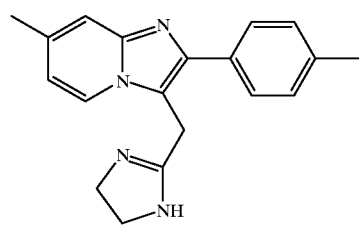

Compound 2

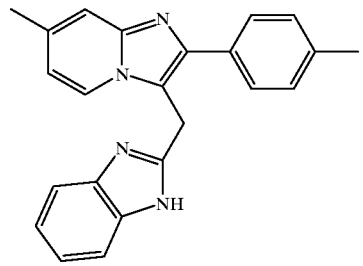

Compound 3

TABLE 1-continued

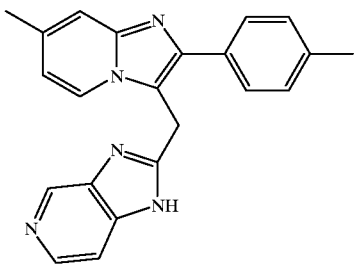

The invention further provides compounds of Formula VI

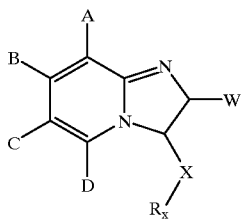

wherein
A, B, C, D and W are as defined for Formula I;
$R_x$ is iminomethoxymethyl, or
$C(O)OR_y$ where $R_y$ represents hydrogen or $C_1$–$C_6$ alkyl.
Preferred compounds of Formula VI are those where
A, C, and D are hydrogen;
B is hydrogen, halogen, $C_1$–$C_3$ alkyl, or $C_1$–$C_3$ alkoxy; and
W is phenyl or pyridyl, each of which is optionally substituted with 1 or 2 groups independently selected from the group consisting of halogen, halo($C_1$–$C_6$)alkyl, hydroxy, amino, $C_1$–$C_6$ alkyl, $C_1$–$C_6$ alkoxy, and mono and di-($C_1$–$C_3$) alkylamino.
Particularly preferred compounds of Formula VI are those where X is methylene and $R_x$ is iminomethoxymethyl. Specific preferred compounds of Formula VI when X is methylene and $R_x$ is iminomethoxymethyl are those where W is optionally substituted phenyl.
Other particularly preferred compounds of Formula VI are those where X is methylene and $R_x$ is $C(O)OR_y$ where $R_x$ is hydrogen.
Still other particularly preferred compounds of Formula VI are those where X is methylene and $R_x$ is $C(O)OR_y$ where $R_y$ is methyl or ethyl. Yet other particularly preferred compounds of Formula VI are those where X is methylene and $R_x$ is $C(O)OR_y$ where $R_y$ is $C_3$–$C_6$ alkyl. Specific preferred compounds of Formula VI when X is methylene and $R_x$ is $C(O)OR_y$ are those where W is optionally substituted phenyl.
Specific compounds of Formula VI include
2-(7-Methyl-2-p-tolyl-imidazo[1,2-a]pyridin-3-yl)-acetimidic acid methyl ester;
(7-Methyl-2-p-tolyl-imidazo[1,2-a]pyridin-3-yl) acetic acid
[7-Chloro-2-(4-chloro-phenyl)-imidazo[1,2-a]pyridin-3-yl) acetic acid
[2-(4-Fluoro-phenyl)-7-methyl-imidazo[1,2-a]pyridin-3-yl) acetic acid
(7-Chloro-2-p-tolyl-imidazo[1,2-a]pyridin-3-yl)acetic acid

[7-Chloro-2-(4-fluoro-phenyl)-imidazo[1,2-a]pyridin-3-yl]acetic acid
[2-(4-Chloro-phenyl)-7-fluoro-imidazo[1,2-a]pyridin-3-yl]acetic acid
[2-(4-Chloro-phenyl)-7-trifluoromethyl-imidazo[1,2-a]pyridin-3-yl)acetic acid
[2-(5-Chloro-pyridin-2-yl)-7-methyl-imidazo[1,2-a]pyridin-3-yl]acetic acid
[7-Methyl-2-(5-methyl-pyridin-2-yl)-imidazo[1,2-a]pyridin-3-yl]acetic acid
[2-(4-Chloro-phenyl)-7-methyl-imidazo[1,2-a]pyridin-3-yl]acetic acid.
The following numbering system is used to identify positions on the imidazo[1,2-a]pyridine ring system of the compounds of the invention:

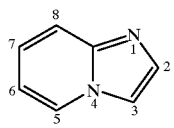

This invention relates to 2-phenylimidazo[1,2-a]pyridine derivatives that bind with high affinity and high selectivity to the benzodiazepine site of $GABA_A$ receptors, including human $GABA_A$ receptors.
The invention also provides pharmaceutical compositions comprising compounds of the invention.
The invention further comprises methods of treating patients in need of such treatment with an amount of a compound of the invention sufficient to alter the symptoms of a CNS disorder.
The diseases and/or disorders that can be treated using compounds and compositions of the invention include
Depression: depression, atypical depression, bipolar disorder, depressed phase of bipolar disorder.
Anxiety: general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclopthymia
Sleep Disorders: sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder
Cognition impairment: cognition impairment, Alzheimer's disease, Parkinson's disease, mild cognitive impairment (MCI), age-related cognitive decline (ARCD), stroke, traumatic brain injury, AIDS associate dementia, dementia associated with depression, anxiety or psychosis.
Compounds of the inventions that act as agonists at $\alpha_2\beta_3\gamma_2$ and $\alpha_3\beta_3\beta_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\beta_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

In a separate aspect, the invention provides a method of potentiating the actions of other CNS active compounds, which comprises administering a therapeutically effective amount of a compound of the invention in combination with another CNS active compound. Such CNS active compounds include, but are not limited to the following: for anxiety, serotonin receptor (e.g. 5-HT$_{1A}$) agonists and antagonists; for anxiety and depression, neurokinin receptor antagonists or corticotropin releasing factor receptor (CRF$_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering a therapeutically effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the GABA$_A$ receptor ligand 3-(5-methylisoxazol-3-yl)-6-(1-methyl-1,2,3-triazol-4-yl) methyloxy-1,2,4-triazolo [3,4-a]phthalzine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of GABA$_A$ receptor ligands, 1,2,4-triazolo[4,3-b]pyridazines, in combination with SSRIs.

This invention also pertains to methods of inhibiting the binding of benzodiazepine compounds, such as Ro15–1788, to the GABA$_A$ receptors which methods involve contacting a compound of the invention with cells expressing GABA$_A$ receptors, wherein the compound is present at a concentration sufficient to inhibit benzodiazepine binding to GABA$_A$ receptors in vitro. This method includes inhibiting the binding of benzodiazepine compounds to GABA$_A$ receptors in vivo, e.g., in a patient given an amount of a compound of Formula I that would be sufficient to inhibit the binding of benzodiazepine compounds to GABA$_A$ receptors in vitro. In one embodiment, such methods are useful in treating benzodiazepine drug overdose. The amount of a compound that would be sufficient to inhibit the binding of a benzodiazepine compound to the GABA$_A$ receptor may be readily determined via a GABA$_A$ receptor binding assay, such as the assay described in Example 6. The GABA$_A$ receptors used to determine in vitro binding may be obtained from a variety of sources, for example from preparations of rat cortex or from cells expressing cloned human GABA$_A$ receptors.

The invention also pertains to methods for altering the signal-transducing activity, particularly the chloride ion conductance, of GABA$_A$ receptors, said method comprising exposing cells expressing such receptors to a therapeutically effective amount of a compound of the invention. This method includes altering the signal-transducing activity of GABA$_A$ receptor s in vivo, e.g., in a patient given an amount of a compound of Formula I that would be sufficient to alter the signal-transducing activity of GABA$_A$ receptors in vitro. The amount of a compound that would be sufficient to alter the signal-transducing activity of GABA$_A$ receptors may be determined via a GABA$_A$ receptor signal transduction assay, such as the assay described in Example 7.

The GABA$_A$ receptor ligands provided by this invention and labeled derivatives thereof are also useful as standards and reagents in determining the ability of a potential pharmaceutical to bind to the GABA$_A$ receptor.

Labeled derivatives the GABA$_A$ receptor ligands provided by this invention are also useful as radiotracers for positron emission tomography (PET) imaging or for single photon emission computerized tomography (SPECT).

More particularly compounds of the invention may be used for demonstrating the presence of GABA$_A$ receptors in cell or tissue samples. This may be done by preparing a plurality of matched cell or tissue samples, at least one of which is prepared as an experiment sample and at least one of which is prepared as a control sample. The experimental sample is prepared by contacting (under conditions that permit binding of RO15-1788 to GABA$_A$ receptors within cell and tissue samples) at least one of the matched cell or tissue samples that has not previously been contacted with any compound or salt of the invention with an experimental solution comprising the detectably-labeled preparation of the selected compound or salt at the first measured molar concentration. The control sample is prepared by in the same manner as the experimental sample and also contains an unlabelled preparation of the same compound or salt of the invention at a greater molar concentration.

The experimental and control samples are then washed to remove unbound detectably-labeled compound. The amount of remaining bound detectably-labeled compound is then measured and the amount of detectably-labeled compound in the experimental and control samples is compared. A comparison that indicates the detection of a greater amount of detectable label in the at least one washed experimental sample than is detected in any of control samples demonstrates the presence of GABA$_A$ receptors in that experimental sample.

The detectably-labeled compound used in this procedure may be labeled with a radioactive label or a directly or indirectly luminescent label. When tissue sections are used in this procedure and the detectably-labeled compound is radiolabeled, the bound, labeled compound may be detected autoradiographically to generate an autoradiogram. The amount of detectable label in an experimental or control sample may be measured by viewing the autoradiograms and comparing the exposure density of the autoradiograms.

The compounds of the invention may have asymmetric centers; this invention includes all of the stereoisomers and optical isomers as well as mixtures thereof.

In addition, compounds with carbon-carbon double bonds may occur in Z- and E- forms; all such isomeric forms of the compounds are included in the invention.

Formula I includes, but is not limited to compounds of Formula II, IIA, III, IIIA, IV, IVA, and V.

Included in the invention are non-toxic pharmaceutically acceptable salts of compounds of general Formula I and the compounds disclosed in the examples which follow. Non-toxic pharmaceutically acceptable salts include, but are not limited to salts with inorganic acids such as hydrochloride, sulfate, phosphate, diphosphate, hydrobromide, and nitrite or salts with an organic acid such as malate, maleate, fumarate, tartrate, succinate, citrate, acetate, lactate, methanesulfonate, p-toluenesulfonate, 2-hydroxyethylsulfonate, salicylate and stearate. Similarly, pharmaceutically acceptable cations include, but are not limited to sodium, potassium, calcium, aluminum, lithium and ammonium.

The invention also encompasses the prodrugs of the compounds of Formula I. Those skilled in the art will recognize various synthetic methodologies that may be employed to prepare non-toxic pharmaceutically acceptable prodrugs of the compounds encompassed by Formula I. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

When any variable (e.g. $C_1$–$C_6$ alkyl, $C_1$–$C_3$ alkyl, A, B, C, D, G, W, X) occurs more than one time in Formula I, its definition on each occurrence is independent of its definition at every other occurrence. Thus, for example, if a group is shown to be substituted with from 0 to three groups $R_n$, then said group may optionally be substituted with up to three $R_n$ groups and $R_n$ at each occurrence is selected independently from the definition of $R_n$. Also, combinations of substituents and/or variables are permissible only if such combinations result in stable compounds.

As used herein, the term "alkyl" indicates alkyl groups of a designed number of carbon atoms, or from 1 to about 8 carbon atoms. Examples of "alkyl" include methyl, ethyl, propyl, isopropyl, butyl, iso-, sec- and tert-butyl, pentyl, hexyl, heptyl, 3-ethylbutyl, cyclopropyl, cyclobutyl, cyclopentyl, cyclohexyl, cycloheptyl, norbornyl, and the like.

The term "alkoxy" indicates an alkyl group of indicated number of carbon atoms, or from 1 to about 8 carbon atoms, attached through an oxygen bridge, such as methoxy, ethoxy, propoxy and isopropoxy.

"Cycloalkyl" is intended to include saturated ring groups, having the specified number of carbon atoms, such as cyclopropyl, cyclobutyl, cyclopentyl, or cyclohexyl. Cycloalkyl groups typically will have 3 to about 8 ring members.

In the term "($C_3$–$C_7$cycloalkyl)C1–$C_4$alkyl", cycloalkyl, and alkyl are as defined above, and the point of attachment is on the alkyl group. This term encompasses, but is not limited to, cyclopropylmethyl, cyclohexylmethyl, and cyclohexylmethyl.

The term "sulfonyl", whether used alone or linked to other terms such as alkylsulfonyl, denotes respectively divalent —$SO_2$— groups. "Alkylsulfonyl" embraces alkyl groups attached to a sulfonyl group, where alkyl is defined as above.

The term "alkylthio" embraces radicals containing an alkyl grouip, defined above, attached to a divalent sulfur atom. An example of "alkylthio" is methylthio, ($CH_3$—S—).

The term "alkylsulfinyl", embraces groups containing an alkyl group, as defined above, attached to a divalent —S(=O)— moiety.

"Alkenyl" is intended to include hydrocarbon chains of either a straight or branched configuration comprising one or more unsaturated carbon-carbon bonds, which may occur in any stable point along the chain, such as ethenyl and propenyl. Alkenyl groups typically will have 2 to about 8 carbon atoms, more typically 2 to about 6 carbon atoms.

"Alkynyl" is intended to include hydrocarbon chains of either a straight or branched configuration comprising one or more carbon-carbon triple bonds, which may occur in any stable point along the chain, such as ethynyl and propynyl. Alkynyl groups typically will have 2 to about 8 carbon atoms, more typically 2 to about 6 carbon atoms.

The term "halogen" or "halo" indicates fluorine, chlorine, bromine, and iodine atoms.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, mono-, di-, or tri-fluoromethyl, mono-, di-, or tri-chloromethyl, mono-, di-, tri-, tetra-, or penta-fluoroethyl, and mono-, di-, tri-, tetra-, or penta-chloroethyl. Typical haloalkyl groups will have 1 to about 8 carbon atoms, more typically 1 to about 6 carbon atoms.

When a group —$NR_yR_z$ is said to form a "3–7 membered heterocyclic ring", the heterocyclic ring may be saturated, partially unsaturated or aromatic and may contain from one to three additional heteroatoms selected from N, O, and S, with remaining ring members being carbon.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups are, for example, phenyl, naphthyl, 1,2,3,[4]-tetrahydronaphthalene, indanyl, and biphenyl. Preferred examples of aryl groups include phenyl and naphthyl. The aryl groups herein are unsubstituted or, as specified, substituted in one or more substitutable positions with various groups.

As used herein, the term "heteroaryl" is intended to include any stable 5-to 7-membered monocyclic or 10- to 14-membered bicyclic ring system, of which at least one ring is aromatic, which monocyclic or bicyclic ring system comprises carbon atoms and from 1 to 4 heteroatoms independently selected from the group consisting of N, O and S. It is preferred that the total number of S and O atoms in the aromatic heterocycle is not more than 2, more preferably not more than 1. Examples of "heteroaryl" groups are thienyl, pyrrolyl, furyl, pyridyl, pyrimidyl, pyrazinyl, pyrazolyl, oxazolyl, isoxazolyl, imidazolyl, thiazolyl, thiazinyl, pyranyl, tetrazolyl, imdazopyrimidinyl, benzimidazolyl, imidazopyridinyl, imidazolopyrazinyl, pyrrolopyrazinyl, pyrrolopyridinyl, indolyl, pteridinyl, pyridinopyrazinyl, pyridinopyridinyl, benzothiazolyl, benzothiazinyl, benzofuranyl, benzothiophenyl, and the like. The heteroaryl groups herein are unsubstituted or, as specified, substituted in one or more substitutable positions with various substituents.

The term or "heterocycloalkyl" is used to refer to saturated heterocyclic rings having at least one ring atom selected from N, O, and S, with remaining atoms being carbon. It is preferred that the total number of heteroatoms in the heterocycloalkyl group is not more than 2. Examples of saturated "heterocycloalkyl" groups are pyrrolidyl, imidazolinyl, imidazolidinyl, piperazinyl, piperidinyl, homopiperazinyl, homopiperidinyl, and morpholinyl. The heterocycloalkyl groups herein are unsubstituted or, as specified, substituted in one or more substitutable positions with various substituents.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches a therapeutically effective concentration is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The invention also pertains to packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

Compound Preparation

An illustration of the preparation of compounds of the invention is given in Schemes I and II.

Scheme I

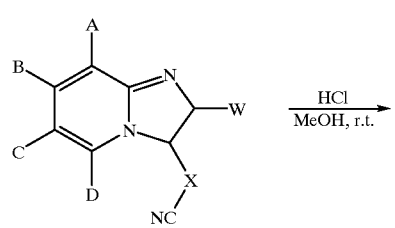

-continued

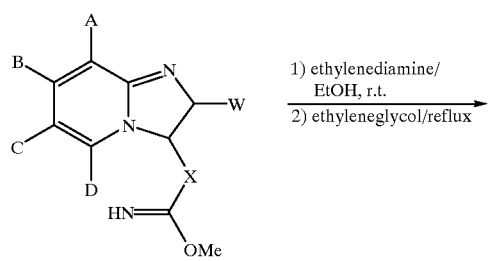

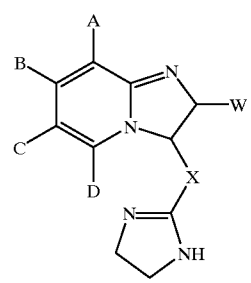

Scheme II

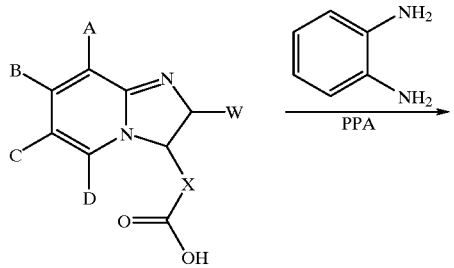

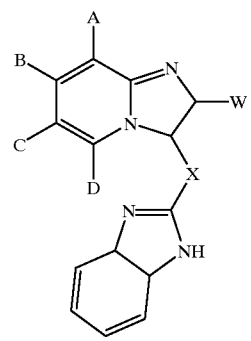

In Schemes I and II, the substituents A, B, C, D, X, and W carry the definitions set forth above for Formula I.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the invention, as demonstrated by the following examples. Unless otherwise stated starting material and reagents employed in this synthesis are of standard commercial grade. In some cases, protection of certain reactive functionalities may be necessary to achieve some of the above transformations. In general, such need for protecting groups, as well as the conditions necessary to attach and remove such groups, will be apparent to those skilled in the art of organic synthesis.

EXAMPLE 1

Synthesis of 3-(4,5-Dihydro-1H-imidazol-2-ylmethyl)-7-methyl-2-p-tolyl-imidazo[1,2-a]Pyridine

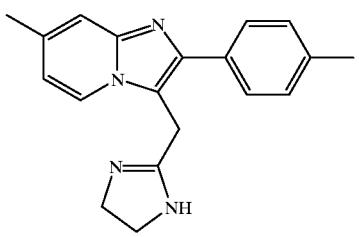

1) 2-[7-methyl-2-(4-methylphenyl)-2-imidazo[1,2-a]pyridin-3-yl)]-1-methoxyethanimine (alternate name: 2-(7-Methyl-2-p-tolyl-imidazo[1,2-a]pyridin-3-yl)-acetimidic acid methyl ester)

A solution of 2-[7-methyl-2-(4-methylphenyl)-2-imidazo[1,2-a]pyridin-3-yl)]ethanenitrile (260 mg, 0.95 mmol) in methanol (40 mL) is saturated with HCl, and then stirred at room temperature for 1 h. Solvent is removed, and the residue is triturated with ether to give the desired product (180 mg, 65%) as an off white solid.

2) 3-(2-imidazolin-2-ylmethyl)-7-methyl-2-(4-methylphenyl)-2-imidazo[1,2-a]pyridine To a solution of the product from step 1 (20 mg, 0.07 mmol) in ethyleneglycol (2 mL) is added ethylenediamine (0.4 mL) and sodium acetate (20 mg). The reaction mixture was heated at 150° C. for 5 h. The reaction solution is cooled to room temperature. Ethyl acetate (10 mL) and water are added to the residue. The organic layer is separated and extracted with hydrochloric acid aqueous solution (1N, 3×10 mL). The combined aqueous layers are neutralized with ammonium hydroxide at 0° C. and extracted with dichloromethane (3×200 mL). The combined organic layers are dried over sodium sulfate, filtered, and concentrated. The product is then isolated by chromatography to give the desired compound, 3-(2-imidazolin-2-ylmethyl)-6-methyl-2-(4-methylphenyl)-2-imidazo[1,2-a]pyridine (6.1 mg, 29%) (compound 1).

LC-MS data: HPLC: 0.61 min (HPLC method: Zorbax XDB-$C_{18}$ column, 4.6×30 mm, 3.5 μm particle size, 3 min. gradient from 0 to 100% B with 0.5 min hold at 100% B. Solvent A: 95% $H_2O$ -5%MeOH-0.05%TFA; Solvent B: 95%MeOH-5%$H_2O$ -0.05% TFA). MS (ES$^+$): m/e 305.14 [MH]$^+$.

EXAMPLE 2

Synthesis of 2-(7-Methyl-2-p-tolyl-imidazo[1,2-a]Pyridin-3-ylmethyl)-1H-benzimidazole

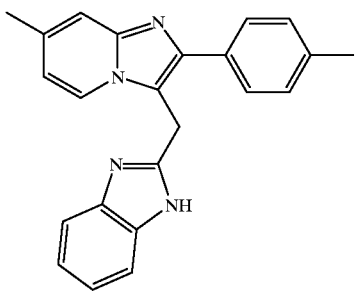

To a solution of 2-[7-methyl-2-(4-methylphenyl)-2-imidazo[1,2-a]pyridin-3-yl)]ethanecarboxylic acid (alternate name: (7-Methyl-2-p-tolyl-imidazo[1,2-a]pyridin-3-yl)acetic acid, 280 mg, 1 mmol) in polyphosphric acid (2 mL) is added phenylenediamine (120 mg) and phosphorus pentoxide (80 mg). The reaction solution is heated at 180° C. under Ar for 2 h. It is then poured into ice water slowly, neutralized with ammonium hydroxide and then extracted with ethyl acetate (3×15 mL). The combined organic layers are dried over $Na_2SO_4$, filtered and concentrated to afford an oily residue. The residue is purified by chromatography to give the title compound, 2-{[6-methyl-2-(4-methylphenyl)-2-imidazo[1,2-a]pyridin-3-yl)]methyl}benzimidazole (21 mg, 6%) (compound 2).

LC-MS data: HPLC: 1.79 min (HPLC method: Zorbax XDB-$C_{18}$ column, 4.6×30 mm, 3.5 μm particle size, 3 min gradient from 0 to 100% B with 0.5 min hold at 100% B. Solvent A: 95% $H_2O$-5% MeOH-0.05% TFA; Solvent B: 95% MeOH-5% $H_2O$ -0.05% TFA). MS (ES$^+$) m/e 353.11 [MH]$^+$.

EXAMPLE 3

The following compounds, shown in TABLE 2 are prepared essentially according to the procedures described in Schemes I–II and further illustrated by Examples 1 and 2:

TABLE 2

| B | G | W | Name |
|---|---|---|---|
| CH₃ | imidazo[4,5-c]pyridin-2-yl | 4-methylphenyl | 2-(7-Methyl-2-p-tolyl-imidazo[1,2-a]pyridin-3-ylmethyl)-1H-imidazo[4,5-c]pyridine (Compound 3) |
| Cl | imidazo[4,5-c]pyridin-2-yl | 4-chlorophenyl | 2-[7-Chloro-2-(4-chlorophenyl)-imidazo[1,2-a]pyridin-3-ylmethyl]-1H-imidazo[4,5-c]pyridine (Compound 4) |
| CH₃ | imidazo[4,5-c]pyridin-2-yl | 4-fluorophenyl | 2-[2-(4-Fluoro-phenyl)-7-methyl-imidazo[1,2-a]pyridin-3-ylmethyl]-1H-imidazo[4,5-c]pyridine (Compound 5) |
| Cl | imidazo[4,5-c]pyridin-2-yl | 4-methylphenyl | 2-(7-Chloro-2-p-tolyl-imidazo[1,2-a]pyridin-3-ylmethyl)-1H-imidazo[4,5-c]pyridine (Compound 6) |
| Cl | imidazo[4,5-c]pyridin-2-yl | 4-fluorophenyl | 2-[7-Chloro-2-(4-fluoro-phenyl)-imidazo[1,2-a]pyridin-3-ylmethyl]-1H-imidazo[4,5-c]pyridine (Compound 7) |

TABLE 2-continued

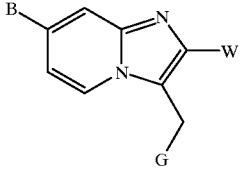

| B | G | W | Name |
|---|---|---|---|
| F |  |  | 2-[2-(4-Chloro-phenyl)-7-fluoro-imidazo[1,2-a]pyridin-3-ylmethyl]-1H-imidazo[4,5-c]pyridine (Compound 8) |
| $CF_3$ |  |  | 2-[2-(4-Chloro-phenyl)-7-trifluoromethyl-imidazo[1,2-a]pyridin-3-ylmethyl]-1H-imidazo[4,5-c]pyridine (Compound 9) |
| $CH_3$ |  |  | 2-[2-(4-Chloro-phenyl)-7-methyl-imidazo[1,2-a]pyridin-3-ylmethyl]-1H-imidazo[4,5-b]pyrazine (Compound 10) |
| $CH_3$ |  |  | 2-(7-Methyl-2-p-tolyl-imidazo[1,2-a]pyridin-3-ylmethyl)-1H-imidazo[4,5-b]pyrazine (Compound 11) |
| $CH_3$ |  |  | 2-[2-(5-Chloro-pyridin-2-yl)-7-methyl-imidazo[1,2-a]pyridin-3-ylmethyl]-1H-imidazo[4,5-c]pyridine (Compound 12) |

TABLE 2-continued

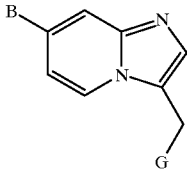

| B | G | W | Name |
|---|---|---|---|
| CH₃ | 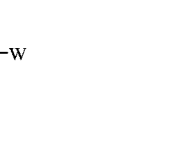 | 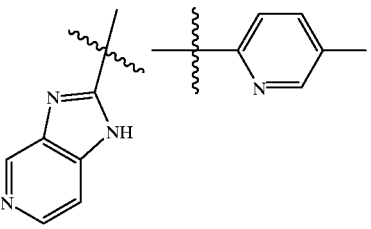 | 2-[7-Methyl-2-(5-methyl-pyridin-2-yl)-imidazo[1,2-a]pyridin-3-ylmethyl]-1H-imidazo[4,5-c]pyridine (Compound 13) |
| CH₃ | 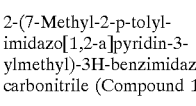 | 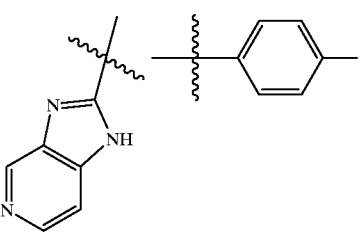 | 2-(7-Methyl-2-p-tolyl-imidazo[1,2-a]pyridin-3-ylmethyl)-3H-benzimidazole-5-carbonitrile (Compound 14) |
| CH₃ | 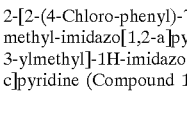 | | 2-[2-(4-Chloro-phenyl)-7 methyl-imidazo[1,2-a]pyridin-3-ylmethyl]-1H-imidazo[4,5-c]pyridine (Compound 15) |

Physical Data for Compound 3:

LC-MS data: HPLC: 1.45 min (HPLC method: Zorbax XDB-$C_{18}$ column, 4.6×30 mm, 3.5 μm particle size, 3 min gradient from 0 to 100% B with 0.5 min hold at 100% B. Solvent A: 95% $H_2O$ -5% MeOH-0.05% TFA; Solvent B: 95% MeOH-5% $H_2O$ -0.05% TFA). MS ($ES^+$): m/e 354.10 $[MH]^+$.

EXAMPLE 4

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^3H$), sulfur (preferably 35S), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 5

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

EXAMPLE 6

Binding Assay

The high affinity and high selectivity of compounds of this invention for the benzodiazepine site of the $GABA_A$ receptor is confirmed using the binding assay described in Thomas and Tallman (*J. Bio. Chem.* 1981; 156:9838–9842, and *J. Neurosci.* 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000× g for 20 minutes. The supernatant is decanted, the pellet rehomogenized in the same volume of buffer, and centrifuged again at 20,000× g. The supernatant of this centrifugation step is decanted and the pellet stored at −20° C. overnight. The pellet is then thawed and resuspended in 25 volumes of Buffer A (original wt/vol), centrifuged at 20,000 × g and the supernatant decanted. This wash step is repeated once. The resulting membrane pellet is finally resuspended in 50 volumes of Buffer A.

Incubations containi 100 μl of membrane pellet, 100 μl of radioligand, (0.5 nM $^3$H-Ro15-1788 [$^3$H-Flumazenil], specific activity 80 Ci/mmol), and test compound or control (see below), and are brought to a total volume of 500 μl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^3$H Ro15-1788 with 10 μM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}$ M to $10^{-5}$ M obtained per curve by the method described above for determining percent inhibition. $K_i$ values are calculated according the Cheng-Prussof equation. When tested in this assay compounds of the invention exihibit $K_i$ values of less than 1 uM, preferred compounds of the invention have $K_i$ values of less than 500 nM and more preferred compounds of the invention have $K_i$ values of less than 100 nM.

EXAMPLE 7

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. Xenopus Laevis oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 μM GABA is applied.

Compounds are evaluated against a GABA concentration that evokes <10% of the maximal evokable GABA current (e.g. 1 μM −9 μM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+ test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the scope of the invention as set forth in the claims. To particularly point out and distinctly claim the subject matter regarded as invention, the following claims conclude this specification.

What is claimed is:

1. A compound of the formula:

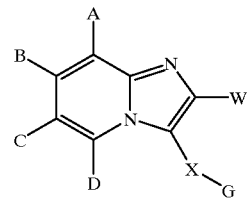

or a pharmaceutically acceptable salt thereof, wherein:
A, B, C, and D independently represent
i) hydrogen, hydroxy, halogen, cyano, nitro,
ii) $C_1$–$C_6$ alkyl optionally substituted independently with one, two, or three of $R_a$,
iii) $C_2$–$C_6$ alkenyl optionally substituted independently with one, two, or three of $R_a$,
iv) $C_2$–$C_6$ alkynyl optionally substituted independently with one, two, or three of $R_a$,
v) $C_1$–$C_6$ alkoxy optionally substituted independently with one, two, or three of $R_a$, vi) alkylthio optionally substituted independently with one, two, or three of $R_a$,
vii) alkylsulfinyl wherein the alkyl portion is optionally substituted independently with one, two, or three of $R_a$,
viii) alkylsulfonyl wherein the alkyl portion is optionally substituted independently with one, two, or three of $R_a$,
ix) —$NR_3R_4$, wherein $R_3$ and $R_4$ are independently hydrogen, $C_1$–$C_6$ alkyl, $C_3$–$C_7$ cycloalkyl, or $C_3$–$C_7$ cycloalkyl ($C_1$–$C_6$)alkyl, and
x) —$NR_3R_4$, wherein $R_3$ and $R_4$ are joined to form a heterocyclic ring having from 3–7 members, where $R_a$ is independently chosen at each occurrence from halogen, hydroxy, $C_1$–$C_6$ alkoxy, nitro, cyano, amino, or oxo, G is imidazolyl, imidazopyridinyl, imidazopyrazinyl, or benzimidazolyl, each of which is optionally substituted with up to three groups independently selected from:
i) halogen, halo($C_1$–$C_6$)alkyl, hydroxy, nitro, cyano,
ii) arylalkyl, wherein the aryl portion of the arylalkyl moiety is optionally substituted with one, two, or three groups which are independently chosen from halogen, nitro, cyano, hydroxy, halo($C_1$–$C_6$)alkyl, amino, mono- and di-alkyl($C_1$–$C_6$)amino,
iii) —$NR_5R_6$ wherein $R_5$ and $R_6$ are the same or different and independently represent hydrogen, alkoxyalkyl, or $C_1$–$C_6$alkyl substituted with —$(CH_2)_m$—$NR_7R_8$, wherein m is 0 or an integer of from 1 to 6 and $R_7$, and $R_8$ are the same or different and represent hydrogen, $C_1$–$C_6$ alkyl, $C_3$–$C_7$cycloalkyl, or $C_3$–$C_7$ cycloalkyl($C_1$–$C_6$)alkyl,
iv) $C_1$–$C_6$ alkyl and $C_1$–$C_6$ alkoxy, each of which is optionally substituted with one or two of $R_b$, and
v) heterocycloalkyl optionally substituted with up to three groups which are independently chosen from halogen, hydroxy, nitro, cyano, halo($C_1$–$C_6$)alkyl, $C_1$–$C_6$alkyl, ($C_1$–$C_6$)alkoxy, ($C_1$–$C_6$)alkoxy ($C_1$–$C_6$)alkyl, ($C_1$–$C_6$) alkoxy ($C_1$–$C_6$)alkoxy, ($C_3$–$C_7$)cycloalkyl ($C_1$–$C_6$) alkoxy, cycloalkyl($C_1$–$C_6$)alkyl, hydroxy($C_1$–$C_6$)alkyl, hydroxy($C_1$–$C_6$)alkoxy, amino($C_1$–$C_6$)alkyl, and phenyl;

W is phenyl or pyridyl, each of which is optionally substituted with one, two, or three groups which are independently chosen from
i) halogen, nitro, cyano, hydroxy, halo($C_1$–$C_6$)alkyl, amino, mono- and di-($C_1$–$C_6$)alkylamino,
ii) $C_1$–$C_6$ alkyl and $C_1$–$C_6$ alkoxy, each of which is optionally substituted with one or two of $R_c$, $R_b$ and $R_c$ are independently chosen at each occurrence from:
i) hydroxy, $C_1$–$C_6$alkoxy, $C_3$–$C_7$cycloalkyl, $C_3$–$C_7$cycloalkyl($C_1$–$C_6$)alkoxy, heterocycloalkyl,
ii) —$(CH_2)_x$—$NR_9R_{10}$, wherein x is 0 or an integer of 1 to 6, and $R_9$ and $R_{10}$ are the same or different and represent hydrogen, $C_1$–$C_6$ alkyl, $C_3$–$C_7$cycloalkyl, or $C_3$–$C_7$ cycloalkyl($C_1$–$C_6$)alkyl, and
iii) —$NR_9R_{10}$, where $R_9$ and $R_{10}$ are joined to form a heterocyclic ring having from 3–7 members; and
X is O, NH, N(C1–$C_6$ alkyl), S, $SO_2$, or $(CH_2)_n$, wherein n is 1, 2, 3, or 4.

2. A compound or salt according to claim 1 wherein:
G is imidazolyl, imidazopyridinyl, imidazopyrazinyl, or benzimidazolyl each of which is optionally substituted with up to three groups independently selected from:
i) halogen, halo($C_1$–$C_6$)alkyl, hydroxy, nitro, cyano,
ii) arylalkyl, wherein the aryl portion of the arylalkyl moiety is optionally substituted with one, two, or three groups which are independently chosen from halogen, nitro, cyano, hydroxy, halo($C_1$–$C_6$)alkyl, amino, mono- and di-alkyl($C_1$–$C_6$) amino,
iii) —$NR_5R_6$ wherein $R_5$ and $R_6$ are the same or different and independently represent hydrogen, alkoxyalkyl, or $C_1$–$C_6$ alkyl substituted with —$(CH_2)_m$—$NR_7R_8$, wherein m is 0 or an integer of from 1 to 6 and $R_7$ and $R_8$ are the same or different and represent hydrogen, $C_1$–$C_6$ alkyl, $C_3$–$C_7$ cycloalkyl, or $C_3$–$C_7$ cycloalkyl($C_1$–$C_6$)alkyl,
iv) $C_1$–$C_6$ alkyl and $C_1$–$C_6$ alkoxy, each of which is optionally substituted with one or two of $R_b$, wherein $R_b$ is as defined in claim 1, and
v) heterocycloalkyl optionally substituted with up to three groups which are independently chosen from halogen, hydroxy, nitro, cyano, halo($C_1$–$C_6$)alkyl, $C_1$–$C_6$alkyl, ($C_1$–$C_6$)alkoxy, ($C_1$–$C_6$)alkoxy($C_1$–$C_6$)alkyl, ($C_1$–$C_6$) alkoxy ($C_1$–$C_6$)alkoxy, ($C_3$–$C_7$)cycloalkyl ($C_1$–$C_6$) alkoxy, cycloalkyl($C_1$–$C_6$)alkyl, hydroxy($C_1$–$C_6$)alkyl, hydroxy ($C_1$–$C_6$)alkoxy, amino($C_1$–$C_6$)alkyl, and phenyl.

3. A compound or salt according to claim 2, wherein
X is methylene; and
G represents

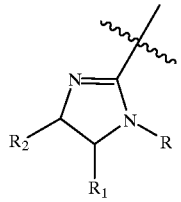

wherein
R represents hydrogen, $C_1$–$C_6$ alkyl, or $C_3$–$C_7$ cycloalkyl; and
$R_1$ and $R_2$ independently represent hydrogen, halogen, $C_1$–$C_6$alkyl, or $C_1$–$C_6$alkoxy.

4. A compound or salt according to claim 2, wherein
A, C, and D are hydrogen;
B represents hydrogen, halogen, $C_1$–$C_3$ alkyl, or $C_1$–$C_3$ alkoxy;
W is phenyl or pyridyl each of which is optionally substituted with 1 or 2 groups independently selected from the group consisting of halogen, halo($C_1$–$C_6$) alkyl, hydroxy, amino, $C_1$–$C_6$ alkyl, $C_1$–$C_6$ alkoxy, and mono and di-($C_1$–$C_3$) alkylamino; and
G represents

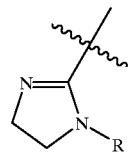

where R represents hydrogen, $C_1$–$C_6$ alkyl, or $C_3$–$C_7$ cycloalkyl.

5. A compound or salt according to claim 2, wherein
X is methylene; and
G represents

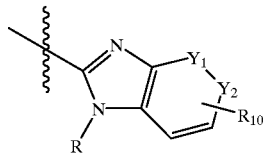

wherein:
R represents hydrogen, $C_1$–$C_6$ alkyl, or $C_3$–$C_7$ cycloalkyl;
$R_{10}$ represents 0, 1, or 2 groups independently selected from
  i) halogen, halo($C_1$–$C_6$)alkyl, hydroxy, nitro, cyano,
  ii) arylalkyl, wherein the aryl portion of the arylalkyl moiety is optionally substituted with one, two, or three groups which are independently selected from halogen, nitro, cyano, hydroxy, halo($C_1$–$C_6$) alkyl, amino, mono- and di-alkyl($C_1$–$C_6$)amino,
  iii) —$NR_5R_6$ wherein $R_5$ and $R_6$ are the same or different and independently represent hydrogen, alkoxyalkyl, or $C_1$–$C_6$ alkyl substituted with —$(CH_2)_m$—$NR_7R_8$, wherein m is 0 or an integer of from 1 to 6 and $R_7$ and $R_8$ are the same or different and represent hydrogen, $C_1$–$C_6$ alkyl, $C_3$–$C_7$ cycloalkyl, or $C_3$–$C_7$ cycloalkyl($C_1$–$C_6$) alkyl, and
  iv) $C_1$–$C_6$ alkyl and $C_1$–$C_6$ alkoxy, each of which is optionally substituted with one or two of $R_b$, and
  v) heterocycloalkyl optionally substituted with up to three groups which are independently selected from halogen, hydroxy, nitro, cyano, halo($C_1$–$C_6$) alkyl, $C_1$–$C_6$alkyl, ($C_1$–$C_6$)alkoxy, ($C_1$–$C_6$)alkoxy ($C_1$–$C_6$)alkyl, ($C_1$–$C_6$)alkoxy ($C_1$–$C_6$)alkoxy, ($C_3$–$C_7$)cycloalkyl ($C_1$–$C_6$)alkoxy, cycloalkyl ($C_1$–$C_6$)alkyl, hydroxy($C_1$–$C_6$)alkyl, hydroxy ($C_1$–$C_6$)alkoxy, amino ($C_1$–$C_6$)alkyl, and phenyl; and
$Y_1$ and $Y_2$ represent CH or N, with the proviso that not both $Y_1$ and $Y_2$ are N.

6. A compound or salt according to claim 5, wherein
A, C, and D are hydrogen;
B is hydrogen, halogen, $C_1$–$C_3$ alkyl, or $C_1$–$C_3$ alkoxy;
R represents hydrogen, $C_1$–$C_6$ alkyl, or $C_3$–$C_7$ cycloalkyl;
$R_{10}$ is hydrogen, halogen, halo($C_1$–$C_6$)alkyl, hydroxy, amino, $C_1$–$C_6$ alkyl, $C_1$–$C_6$ alkoxy, or mono or di-($C_1$–$C_3$)alkylamino; and
W is phenyl or pyridyl each of which is optionally substituted with 1 or 2 groups independently selected from the group consisting of halogen, halo($C_1$–$C_6$) alkyl, hydroxy, amino, $C_1$–$C_6$ alkyl, $C_1$–$C_6$ alkoxy, and mono and di-($C_1$–$C_3$) alkylamino.

7. A compound or salt according to claim 2, wherein
X is methylene;
G represents

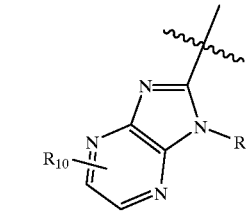

wherein:
R represents hydrogen, $C_1$–$C_6$ alky, or $C_3$–$C_7$ cycloalkyl; and
$R_{10}$ represents 0, 1, or 2 groups independently selected from
  i) halogen, halo($C_1$–$C_6$)alkyl, hydroxy, nitro, cyano,
  ii) arylalkyl, wherein the aryl portion of the arylalkyl moiety is optionally substituted with one, two, or three groups which are independently selected from halogen, nitro, cyano, hydroxy, halo($C_1$–$C_6$) alkyl, amino, mono- and di-alkyl($C_1$–$C_6$)amino,
  iii) —$NR_5R_6$ wherein $R_5$ and $R_6$ are the same or different and independently represent hydrogen, alkoxyalkyl, or $C_1$–$C_6$ alkyl substituted with —$(CH_2)_m$—$NR_7R_8$, wherein m is 0 or an integer of from 1 to 6 and $R_7$ and $R_8$ are the same or different and represent hydrogen, $C_1$–$C_6$ alkyl, $C_3$–$C_7$ cycloalkyl, or $C_3$–$C_7$ cycloalkyl($C_1$–$C_6$) alkyl, and
  iv) $C_1$–$C_6$ alkyl and $C_1$–$C_6$ alkoxy, each of which is optionally substituted with one or two of $R_b$, and
  v) heterocycloalkyl optionally substituted with up to three groups which are independently selected from halogen, hydroxy, nitro, cyano, halo($C_1$–$C_6$) alkyl, $C_1$–$C_6$alkyl, ($C_1$–$C_6$)alkoxy, ($C_1$–$C_6$)alkoxy ($C_1$–$C_6$)alkyl, ($C_1$–$C_6$)alkoxy ($C_1$–$C_6$)alkoxy, ($C_3$–$C_7$)cycloalkyl ($C_1$–$C_6$)alkoxy, cycloalkyl ($C_1$–$C_6$)alkyl, hydroxy ($C_1$–$C_6$)alkyl, hydroxy ($C_1$–$C_6$)alkoxy, amino($C_1$–$C_6$)alkyl, and phenyl.

8. A compound or salt according to claim 7, wherein
A, C, and D are hydrogen;
B is hydrogen, halogen, $C_1$–$C_3$ alkyl, or $C_1$–$C_3$ alkoxy;
R represents hydrogen, $C_1$–$C_6$ alkyl, or $C_3$–$C_7$ cycloalkyl;
$R_{10}$ is hydrogen, halogen, halo($C_1$–$C_6$)alkyl, hydroxy, amino, $C_1$–$C_6$ alkyl, $C_1$–$C_6$ alkoxy, or mono or di-($C_1$–$C_3$)alkylamino; and
W is phenyl or pyridyl each of which is optionally substituted with 1 or 2 groups independently selected from the group consisting of halogen, halo($C_1$–$C_6$) alkyl, hydroxy, amino, $C_1$–$C_6$ alkyl, $C_1$–$C_6$ alkoxy, and mono and di-($C_1$–$C_3$) alkylamino.

9. A compound or salt according to claim 2, wherein
X is methylene;

G represents

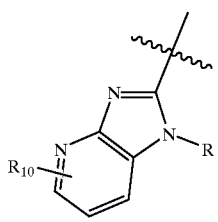

wherein

R represents hydrogen, $C_1$–$C_6$ alkyl, or $C_3$–$C_7$ cycloalkyl;

$R_{10}$ is hydrogen, halogen, halo($C_1$–$C_6$)alkyl, hydroxy, amino, $C_1$–$C_6$ alkyl, $C_1$–$C_6$ alkoxy, or mono or di-($C_1$–$C_3$)alkylamino; and W is phenyl or pyridyl each of which is optionally substituted with 1 or 2 groups independently selected from the group consisting of halogen, halo($C_1$–$C_6$) alkyl, hydroxy, amino, $C_1$–$C_6$ alkyl, $C_1$–$C_6$ alkoxy, and mono and di-($C_1$–$C_3$)alkylamino.

10. A compound according to claim 1, which is 3-(4,5-Dihydro-1H-imidazol-2-ylmethyl)-7-methyl-2-p-tolyl-imidazo[1,2-a]pyridine, or a pharmaceutically acceptable salt thereof.

11. A compound according to claim 1, which is 2-(7-Methyl-2-p-tolyl-imidazo[1,2-a]pyridin-3-ylmethyl)-1H-benzimidazole, or a pharmaceutically acceptable salt thereof.

12. A compound according to claim 1, which is 2-(7-Methyl-2-p-tolyl-imidazo[1,2-a]pyridin-3-ylmethyl)-1H-imidazo[4,5-c]pyridine, or a pharmaceutically acceptable salt thereof.

13. A compound according to claim 1, which is 2-[7-Chloro-2-(4-chloro-phenyl)-imidazo[1,2-a]pyridin-3-ylmethyl]-1H-imidazo[4,5-c]pyridine, or a pharmaceutically acceptable salt thereof.

14. A compound according to claim 1, which is 2-[2-(4-Fluoro-phenyl)-7-methyl-imidazo[1,2-a]pyridin-3-ylmethyl]-1H-imidazo[4,5-c]pyridine, or a pharmaceutically acceptable salt thereof.

15. A compound according to claim 1, which is 2-{[6-chloro- 2-(4-methylphenyl)-3a-hydroimidazolo[1,2-a] pyridin-yl]methyl}imidazolo[4,5-c]pyridine, or a pharmaceutically acceptable salt thereof.

16. A compound according to claim 1, which is 2-[7-Chloro-2-(4-fluoro-phenyl)-imidazo[1,2-a]pyridin-3-ylmethyl]-1H-imidazo[4,5-c]pyridine, or a pharmaceutically acceptable salt thereof.

17. A compound according to claim 1, which is 2-[2-(4-Chloro-phenyl)-7-fluoro-imidazo[1,2-a]pyridin-3-ylmethyl]-1H-imidazo[4,5-c]pyridine, or a pharmaceutically acceptable salt thereof.

18. A compound according to claim 1, which is 2-[2-(4-Chloro-phenyl)-7-trifluoromethyl-imidazo[1,2-a]pyridin-3-ylmethyl]-1H-imidazo[4,5-c]pyridine, or a pharmaceutically acceptable salt thereof.

19. A compound according to claim 1, which is 2-[2-(4-Chloro-phenyl)-7-methyl-imidazo[1,2-a]pyridin-3-ylmethyl]-1H-imidazo[4,5-b]pyrazine, or a pharmaceutically acceptable salt thereof.

20. A compound according to claim 1, which is 2-(7-Methyl-2-p-tolyl-imidazo[1,2-a]pyridin-3-ylmethyl)-1H-imidazo[4,5-b]pyrazine, or a pharmaceutically acceptable salt thereof.

21. A compound according to claim 1, which is 2-[2-(5-Chloro-pyridin-2-yl)-7-methyl-imidazo[1,2-a]pyridin-3-ylmethyl]-1H-imidazo[4,5-c]pyridine, or a pharmaceutically acceptable salt thereof.

22. A compound according to claim 1, which is 2-[7-Methyl-2-(5-methyl-pyridin-2-yl)-imidazo[1,2-a]pyridin-3-ylmethyl]-1H-imidazo[4,5-c]pyridine, or a pharmaceutically acceptable salt thereof.

23. A compound according to claim 1, which is 2-(7-Methyl-2-p-tolyl-imidazo[1,2-a]pyridin-3-ylmethyl)-3H-benzimidazole-5-carbonitrile, or a pharmaceutically acceptable salt thereof.

24. A compound according to claim 1, which is 2-[2-(4-Chloro-phenyl)-7-methyl-imidazo[1,2-a]pyridin-3-ylmethyl]-1H-imidazo[4,5-c]pyridine, or a pharmaceutically acceptable salt thereof.

25. A pharmaceutical composition comprising a compound or salt according to claim 1 combined with at least one pharmaceutically acceptable carrier or excipient.

* * * * *